United States Patent [19]

Simpson et al.

[11] Patent Number: 5,149,620
[45] Date of Patent: Sep. 22, 1992

[54] POST PROCESSING STABILIZED PHOTOTHERMOGRAPHIC EMULSIONS

[75] Inventors: Sahron M. Simpson; John R. Boon; Marco Bucci; Massimo Bertoldi; Cristina Soncini; Kumars Sakizadeh, all of St. Paul, Minn.

[73] Assignee: Minnesota Mining and Manufacturing Company, St. Paul, Minn.

[21] Appl. No.: 559,619

[22] Filed: Jul. 30, 1990

[51] Int. Cl.$^5$ ............................................. G03C 1/02
[52] U.S. Cl. .................................. 430/617; 430/353; 430/607; 430/611; 430/613; 430/620
[58] Field of Search ............... 430/617, 607, 611, 613, 430/353, 620

[56] References Cited

U.S. PATENT DOCUMENTS

| 4,138,265 | 2/1979 | Shiao | 96/114.1 |
| 4,425,033 | 1/1981 | Eida et al. | 430/353 |
| 4,451,561 | 5/1984 | Hirabayashi et al. | 430/619 |
| 4,559,290 | 12/1985 | Sawada et al. | 430/223 |
| 4,837,141 | 6/1989 | Kohno et al. | 430/559 |

Primary Examiner—Charles L. Bowers, Jr.
Assistant Examiner—Thorl Chea
Attorney, Agent, or Firm—Gary L. Griswold; Walter N. Kirn; Mark A. Litman

[57] ABSTRACT

The addition of certain 5-mercapto-1,2,4-triazoles to silver halide photothermographic emulsions improves the post-processing image stability of those emulsions.

15 Claims, No Drawings

POST PROCESSING STABILIZED PHOTOTHERMOGRAPHIC EMULSIONS

FIELD OF THE INVENTION

This invention relates to photothermographic materials and in particular to post-processing stabilization of dry silver systems.

BACKGROUND OF THE ART

Silver halide photothermographic imaging materials, especially "dry silver" compositions, processed with heat and without liquid development have been known in the art for many years. Such materials are a mixture of light insensitive silver salt of an organic acid (e.g., silver behenate), a minor amount of catalytic light sensitive silver halide, and a reducing agent for the silver source.

The light sensitive silver halide is in catalytic proximity to the light insensitive silver salt such that the latent image formed by the irradiation of the silver halide serves as a catalyst nucleus for the oxidation-reduction reaction of the organic silver salt with the reducing agent when heated above 80° C. Such media are described in U.S. Pat. Nos. 3,457,075; 3,839,049; and 4,260,677. Toning agents can be incorporated to improve the color of the silver image of photothermographic emulsions as described in U.S. Pat. Nos. 3,846,136; 3,994,732 and 4,021,249. Various methods to produce dye images and multicolor images with photographic color couplers and leuco dyes are well known in the art as represented by U.S. Pat. Nos. 4,022,617; 3,531,286; 3,180,731; 3,761,270; 4,460,681; 4,883,747 and Research Disclosure 29963.

A common problem that exists with these photothermographic systems is the instability of the image following processing. The photoactive silver halide still present in the developed image may continue to catalyze print-out of metallic silver even during room light handling. Thus, there exists a need for stabilization of the unreacted silver halide with the addition of separate post-processing image stabilizers or stabilizer precursors to provide the desired post-processing stability. Most often these are sulfur containing compounds such as mercaptans, thiones, thioethers and development inhibitor releasing compounds as described in Research Disclosure 17029 and U.S. Pat. No. 3,700,457. Examples of stabilizer precursors in photothermographic materials are described in U.S. Pat. Nos. 3,839,041 and 3,301,678. U.S. Pat. Nos. 4,351,896 and 4,404,390 describe the use of blocked mesoionic 1,2,4-triazolium-3-thiolates as silver halide stabilizer precursors in which the sulfur atom is blocked by an appropriate blocking group which is cleaved upon processing at processing temperatures to provide a moiety that combines with the photoactive silver halide in the unexposed and undeveloped areas of the photographic material. The resulting silver mercaptide is more stable than silver halide to light, atmospheric and ambient conditions. However, one of the problems with stabilizer precursurs is the inadequate release of the stabilizing moiety within the desired time frame during processing.

Specifically, in connection with this invention, U.S. Pat. No. 4,245,033 describes sulfur compounds of the mercapto-type that are development restrainers of photothermographic systems. The use of substituted 5-mercapto-1,2,4-triazoles with immobilizing groups that are of a ballasting polymer type or hydrophilic in nature such as sulfo, hydroxyl, carboxyl or sulfonic acid as development restrainers are also described in U.S. Pat. No. 4,837,141. Mesoionic 1,2,4-triazolium-3-thiolates as fixing agents and silver halide stabilizers are described in U.S. Pat. No. 4,378,424. Substituted 5-mercapto-1,2,4-triazoles such as 3-amino-5-benzothio-1,2,4-triazole as post-processing stabilizers are described in U.S. Pat. No. 4,128,557; 4,137,079; 4,138,265; and Research Disclosures 16977 and 16979. U.S. Pat. No. 4,451,561 describes amido derivatives of 5-mercapto-1,2,4-triazoles as development restrainers.

Some of the problems with these stabilizers include thermal fogging during processing or losses in photographic sensitivity, maximum density or contrast at stabilizer concentrations in which stabilization of the post-processed image can occur. Thus, there has been a continued need for improved post-processing stabilizers which stabilize the photoactive silver halide for post-processing stabilization without desensitizing or fogging the photographic materials.

SUMMARY OF THE INVENTION

According to this invention, the incorporation of electron-withdrawing groups on the 3-position of 5-mercapto-1,2,4-triazoles to the photothermographic emulsion layer or a layer adjacent to the emulsion layer stabilizes the photoactive silver halide for improved post-processing stabilization without desensitizing or fogging the heat developable photographic material and process. These compounds are described in Formula I:

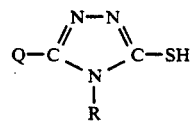

wherein
R represents hydrogen, alkyl (preferably of 1 to 12 carbon atoms, substituted or not), aryl (preferably up to 20 carbon atoms, substituted or not), or aralkyl (preferably up to 20 carbon atoms, substituted or not), and
Q represents an electron-withdrawing group at least as electron withdrawing as $CF_3(CH_2)hd 6-$.
Q is preferably a group of the formula

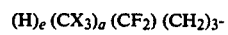

where
a is 0 or 1,
b is 0 or between 1 and 6,
c is 0 or between 1 and 20,
d is 0 or between 1 and 6,
e is 0 when a is 1 and e is 1 when a is zero, and
a plus c is at least one and
b plus d is no more than 6.

More preferably b and d are zero and a plus c is between 1 and 20. X is a halogen atom, preferably F, Br, and Cl, and most preferably comprises F. Mixtures of halogen atoms, particularly where F predominates and a minor proportion of Cl or Br are present are of course useful and contemplated in the present invention. Perfluorinated groups are preferred. The shorter chain perfluorinated groups are generally preferred for their cost and manufacturing considerations, but the long chain perfluorinated group may have an advantage in their compatibility or ease of solubility in the fatty acid materials with which they may be associated. The tautomeric form of structural formula I is also included within the formula. In that structure the external hydrogen is shifted to the adjacent nitrogen atom and the double bonds shift to accommodate the positioning of the hydrogen atom.

It is another aspect of the present invention that excellent preservability occurs in both the developed post-processing image and the unexposed photothermographic layer in the photothermographic element without desensitization of the element or the processed image.

DETAILED DESCRIPTION OF THE INVENTION

The addition of electron-withdrawing groups on the 3-position of 5-mercapto-1,2,4 triazoles present in a silver halide photothermographic emulsion or the adjacent layer to the emulsion provides the emulsion with improved post-processing stability and unexposed Dmin stability without fogging or desensitizing said emulsion. Specific examples of the substituted 5-mercapto-1,2,4 triazoles are shown by the formula below, which, however, does not limit the compounds to be used in the present invention.

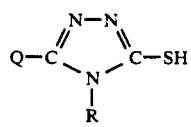

| Compound | Q | R |
|---|---|---|
| I-A | $CF_3-$ | $-CH_3$ |
| I-B | $CF_3CF_2-$ | $-CH_3$ |
| I-C | $CF_3(CF_2)_{19}-$ | $-CH_3$ |
| I-D | $CH_3(CF_2)_6-$ | $-CH_3$ |
| I-E | $CF_3(CF_2)_3-$ | H |
| I-F | $CF_3CF_2(CH_2)_6-$ | $-C_6H_5$ |
| I-G | $CF_3-$ | $-C_6H_4CH_3$ |
| I-H | $CF_2Cl-$ | $CH_3$ |
| I-I | $CF_3$ | $CH_3CH_2OCH_2CH_2-$ |
| I-J | $CF_3$ | $CH_3(CH_2)_5-$ |

Synthesis of Compound I-A (3-trifluoromethyl-4-methyl-5-mercapto-1,2,4 triazole)

This exemplified compound may be readily synthesized by the reaction of methyl isocyanate with hydrazine to give 4-methyl-3-thiosemicarbazide followed by cyclocondensation with trifluoroacetic acid as described in U.S. Pat. No. 4,477,459. This compound may also be prepared by the reaction of 4-methyl-3-thiosemicarbazide with trifluoroacetylfluoride and heat (U.S. Pat. No. 3,780,052).

The synthesis of the comparative compound in Example 1A is shown below.

Synthesis of 3,4-dimethyl-5-mercapto-1,2,4-triazole

4-Methyl-3-thiosemicarbazide (10.5 g, 0.1 mole) was dissolved in acetic anhydride (30 ml). A white precipitate was formed which after filtration and drying had m.p. 165° C. The precipitate was then heated up to its melting point and kept at that temperature for 5-10 minutes. After cooling to room temperature, the solid obtained was crystallized from hot water to give the desired product in a 60% yield (5.16 g).

The amounts of the above described compounds (e.g., I-A) according to the present invention which are added can be varied depending upon the particular compound used and upon the photothermographic emulsion-type. However, they are preferably added in an amount of $10^{-3}$ to 10 mol, and more preferably from $10^{-2}$ to 3 mol, per mol of silver halide in the emulsion layer.

The photothermographic dry silver emulsions of this invention may be constructed of one or more layers on a substrate. Single layer constructions must contain the silver source material, the silver halide, the developer and binder as well as optional additional materials such as toners, coating aids and other adjuvants. Two-layer constructions must contain the silver source and silver halide in one emulsion layer (usually the layer adjacent the substrate) and some of the other ingredients in the second layer or both layers. Multicolor photothermographic dry silver constructions contain sets of these bilayers for each color. Color forming layers are maintained distinct from each other by the use of functional or non-functional barrier layers between the various photosensitive layers as described in U.S. Pat. No. 4,460,681.

The silver source material, as mentioned above, may be any material which contains a reducible source of silver ions. Silver salts of organic acids, particularly long chain (10 to 30, preferably 15 to 28 carbon atoms) fatty carboxylic acids are preferred. Complexes of organic or inorganic silver salts wherein the ligand has a gross stability constant between 4.0 and 10.0 are also desirable. The silver source material constituents from about 5 to 30 percent by weight of the imaging layer. The second layer in a two-layer construction or in the bilayer of a multi-color construction would not affect the percentage of the silver source material desired in the photosensitive single imaging layer.

The organic silver salt which can be used in the present invention is a silver salt which is comparatively stable to light, but forms a silver image when heated to 80° C. or higher in the presence of an exposed photocatalyst (such as silver halide) and a reducing agent.

Suitable organic silver salt include silver salts of organic compounds having a carboxy group. Preferred examples thereof include a silver salt of an aliphatic carboxylic acid and a silver salt of an aromatic carboxylic acid. Preferred examples of the silver salts of aliphatic carboxylic acids include silver behenate, silver stearate, silver oleate, silver laurate, silver caprate, silver myristate, silver palmitate, silver maleate, silver fumarate, silver tartarate, silver furoate, silver linoleate, silver butyrate and silver camphorate, mixtures thereof, etc. Silver salts which are suitable with a halogen atom of a hydroxyl group can also be effectively used. Preferred examples of the silver salts of aromatic carboxylic acid and other carboxyl group-containing compounds include silver benzoate, a silver substituted benzoate such as silver 3,5-dihydroxybenzoate, silver o-methylbenzoate, silver m-methylbenzoate, silver p-methylbenzoate, silver 2,4-dichlorobenzoate, silver acetamidobenzoate, silver p-phenyl benzoate, etc., silver gallate, silver tannate, silver phthalate, silver terephthalate, silver salicylate, silver phenylacetate, silver pyromellitate, a silver salt of 3-carboxymethyl-4-methyl-4-thiazoline-2-thione or the like as described in U.S. Pat. No. 3,785,830, and silver salt of an aliphatic carboxylic acid containing a thioether group as described in U.S. Pat. No. 3,330,663, etc.

Silver salts of compounds containing mercapto or thione groups and derivatives thereof can be used. Preferred examples of these compounds include a silver salt of 3-mercapto-4-phenyl-1,2,4-triazole, a silver salt of 2-mercaptobenzimidazole, a silver salt of 2-mercapto-5-aminothiadiazole, a silver salt of 2-(s-ethylglycolamido) benzothiazole, a silver salt of thioglycolic acid such as a silver salt of a S-alkyl thioglycolic acid (wherein the alkyl group has from 12 to 22 carbon atoms) as described in Japanese patent application No. 28221/73, a silver salt of a dithiocarboxylic acid such as a silver salt of dithioacetic acid, a silver salt of thioamide, a silver salt of 5-carboxylic-1-methyl-2-phenyl-4-thiopyridine, a silver salt of mercaptotriazine, a silver salt of 2-mercaptobenzoxazole, a silver salt as described in U.S. Pat. No. 4,123,274, for example, a silver salt of 1,2,4-mercaptothiazole derivative such as a silver salt of 3-amino-5-benzylthio-1,2,4-thiazole, a silver salt of thione compound such as a silver salt of 3-(2-carboxyethyl)-4-methyl-4-thiazoline-2-thione as disclosed in U.S. Pat. No. 3,301,678.

Furthermore, a silver salt of a compound containing an imino group can be used. Preferred examples of these compounds include a silver salt of benzothiazole and a derivative thereof as described in Japanese patent publications Nos. 30270/69 and 18146/70, for example, a silver salt of benzothiazole such as silver salt of methylbenzotriazole, etc., a silver salt of a halogen substituted benzotriazole, such as a silver salt of 5-chlorobenzotriazole, etc., a silver salt of carboimidobenzotriazole, etc., a silver salt of 1,2,4-triazole, of 1-H-tetrazole as described in U.S. Pat. No. 4,220,709, a silver salt of imidazole and an imidazole derivative, and the like.

It is also found convenient to use silver halfsoaps, of which an equimolar blend of silver behenate and behenic acid, prepared by precipitation from aqueous solution of the sodium salt of commercial behenic acid and analyzing about 14.5 percent silver, represents a preferred example. Transparent sheet materials made on transparent film backing require a transparent coating and for this purpose the silver behenate full soap, containing not more than about 4 or 5 percent of free behenic acid and analyzing about 25.2 percent silver may be used.

The method used for making silver soap dispersions is well known in the art and is disclosed in Research Disclosure April 1983 (22812) ibid October 1983 (23419) and U.S. Pat. No. 3,985,565.

The light sensitive silver halide used in the present invention can be employed in a range of 0.0005 mol to 5 mol and, preferably, from 0.005 mol to 1.0 mol per mol of organic silver salt.

The silver halide may be any photosensitive silver halide such as silver bromide, silver iodide, silver chloride, silver bromoiodide, silver chlorobromoiodide, silver chlorobromide, etc.

The silver halide used in the present invention may be employed without modification. However, it may be chemically sensitized with a chemical sensitizing agent such as a compound containing sulphur, selenium or tellurium etc., or a compound containing gold, platinum, palladium, rhodium or iridium, etc., a reducing agent such as a tin halide, etc., or a combination thereof. The details of these procedures are described in T.H. James "The Theory of the Photographic Process", Fourth Edition, Chapter 5, pages 149 to 169.

The silver halide may be added to the emulsion layer in any fashion which places it in catalytic proximity to the silver source.

The silver halide and the organic silver salt which are separately formed in a binder can be mixed prior to use to prepare a coating solution, but it is also effective to blend both of them in a ball mill for a long period of time. Further, it is effective to use a process which comprises adding a halogen-containing compound in the organic silver salt prepared to partially convert the silver of the organic silver salt to silver halide.

Methods of preparing these silver halide and organic silver salts and manners of blending them are described in Research Disclosures, No. 170-29, Japanese patent applications No. 32928/75 and 42529/76, U.S. Pat. No. 3,700,458, and Japanese patent applications Nos. 13224/74 and 17216/75.

The use of preformed silver halide emulsions of this invention can be unwashed or washed to remove soluble salts. In the latter case the soluble salts can be removed by chill-setting and leaching or the emulsion can be coagulation washed, e.g., by the procedures described in Hewitson, et al., U.S. Pat. No. 2,618,556; Yutzy et al., U.S. Pat. No. 2,614,928; Yackel, U.S. Pat. No. 2,565,418;; Hart et al., U.S. Pat. No. 3,241,969; and Waller et al., U.S. Pat. No. 2,489,341. The silver halide grains may have any crystalline habit including, but not limited to cubic, tetrahedral, orthorhombic, tabular, laminar, platelet, etc.

Photothermographic emulsions containing preformed silver halide in accordance with this invention can be sensitized with chemical sensitizers, such as with reducing agents; sulfur, selenium or tellurium compounds; gold, platinum or palladium compounds, or combinations of these. Suitable chemical sensitization procedures are described in Shepard, U.S. Pat. No. 1,623,499; Waller, U.S. Pat. No. 2,399,083; McVeigh, U.S. Pat. No. 3,297,447; and Dunn, U.S. Pat. No. 3,297,446.

The light-sensitive silver halides can be spectrally sensitized with various known dyes include cyanine, styryl, hemicyanine, oxonol, hemioxonol and xanthene dyes. Useful cyanine dyes include those having a basic nucleus, such as a thiazoline nucleus, an oxazoline nucleus, a pyrroline nucleus, a pyridine nucleus, an oxazole nucleus, a thiazole nucleus, a selenazole nucleus and an imidazole nucleus. Useful merocyanine dyes which are preferred include those having not only the above described basic nuclei but also acid nuclei, such as a thiohydantoin nucleus, a rhodanine nucleus, an oxazolidinedione nucleus, a thiazolidinedione nucleus, a barbituric acid nucleus, a thiazolinone nucleus, a malonitrile nucleus and a pyrazolone nucleus. In the above described cyanine and merocyanine dyes, those having imino groups or carboxyl groups are particularly effective. Practically, the sensitizing dyes to be used in the present invention is properly selected from known dyes as described in U.S. Pat. No. 3,761,279, 3,719,495 and 3,877,943, British Pat Nos. 1,466,201, 1,469,117 and 1,422,057, Japanese Patent Application (OPI) Nos. 27924/76 and 156424/75, and so on, and can be located in the vicinity of the photocatalyst according to known methods used in the above-described examples. These spectral sensitizing dyes are used in amounts of about $10^{-4}$ mol to about 1 mol per 1 mol of photocatalyst.

The reducing agent for silver ion may be any material, preferably organic material, which will reduce silver ion and metallic silver. Conventional photographic developers such as phenidone, hydroquinones, and catechol are useful but hindered phenol reducing agents are preferred. The reducing agent should be present as 1 to 10 percent by weight of the imaging layer. In a two-layer construction, if the reducing agent is in the second layer, slightly high proportions, of from about 2 to 15 percent tend to be more desirable.

A wide range of reducing agents have been disclosed in dry silver systems including amidoximes such as phenylamidoxime, 2-thienylamidoxime and p-phenoxyphenylamidoxime, azine, e.g., 4-hydroxy-3,5-dimethoxybenzaldehyde azine; a combination of aliphatic carboxylic acid aryl hydrazides and ascorbic acid, such as 2,2-bis(hydroxymethyl)propionyl-beta-phenyl hydrazide in combination with ascorbic acid; a combination of polyhydroxybenzene and hydroxylamine, a reductone and/or a hydrazine, e.g., a combination of hydroquinone and bis(ethoxyethyl)hydroxylamine, piperidinohexose reductone or formyl-4-methylphenyl hydrazine, hydroxamic acids such as phenylhydroxamic acid, p-hydroxyphenyl hydroxamic acid, and beta-alanine hydroxamic acid; a combination of azines and sulphonamidophenols, e.g., phenothiazine and 2,6-dichloro-4-benzenesulphonamidophenol; alphacyanophenylacetic acid derivatives such as ethyl-alphacyano-2-methylphenylacetate, ethyl alphacyanophenylacetate; bis-beta-naphthols as illustrated by 2,2'-dihydroxy-1,1,-binaphthyl, 6,6'-dibromo-2,2'-dihydroxy-1,1'-binaphthyl, and bis(2-hydroxy-1-naphthyl)methane; a combination of bis-beta-naphthol and a 1,3-dihydroxybenzene derivative, e.g., 2,4-dihydroxybenzophenone or 2,4,-dihydroxyacetophenone; 5-pyrazolones such as 3-methyl-1-phenyl-5-pyrazolone; reductones as illustrated by dimethylamino hexose reductone, anhydro dihydro amino hexose reductone, and anhydro dihydro piperidone hexose reductone; sulphonamidophenol reducing agents such as 2,6-dichloro-4-benzensulphonamidophenol, and p-benzenesulphonamidophenol; 2-phenylindane-1,3-dione and the like; chromans such as 2,2-dimethyl-7-t-butyl-6-hydroxychroman; 1,4-dihydropyridines such as 2,6-dimethoxy-3,5-dicarbethoxy-1,4-dihydropyridine; bisphenols e.g., bis(2-hydroxy-3-t-butyl-5-methylphenyl)methane, 2,2-bis(4-hydroxy-3-methylphenyl)propane, 4,4-ethylidene-bis(2-tert-butyl-6-methylphenol), and 2,2-bis(3,5-dimethyl-4-hydroxyphenyl)propane; ascorbic acid derivatives, e.g., 1-ascorbylpalmitate, ascorbylstearate and unsaturated aldehydes and ketones, such as benzyl and diacetyl; 3-pyrazolidones and certain indane-1,3-diones.

The literature discloses additives, "toners", which improve the image.

Toner materials may be present, for example, in amounts from 0.1 to 10 percent by weight of all silver bearing components. Toners are well known materials in the photothermographic art as shown in U.S. Pat. No. 3,080,254; 3,847,612 and 4,123,282.

Examples of toners include phthalimide and N-hydroxyphthalimide; cyclic imides such as succinimide, pyrazoline-5-ones, and a quinazolinone, 3-phenyl-2-pyrazoline-5-one, 1-phenylurazole, quinazoline, and 2,4-thiazolidinedione; naphthalimides, e.g., N-hydroxy-1,8-naphthalimide; cobalt complexes, e.g., cobaltic hexamine trifluoroacetate; mercaptans as illustrated by 3-mercapto-1,2,4-triazole, 2,4-dimercaptopyrimidine, 3-mercapto-4,5-diphenyl-1,2,4-triazole and 2,5-dimercapto-1,3,4-thiadiazole; N-(aminomethyl)aryl dicarboximides, e.g. (N-dimethylaminomethyl)-phthalimide, and N-(dimethylaminomethyl)naphthalene-2,3-dicarboximide; and a combination of blocked pyrazoles, isothiuronium derivatives and certain photobleach agents, e.g., a combination of N,N'-hexamethylene bis(1-carbamoyl-3,5-dimethylpyrazole), 1,8-(3,6-diazaoctane)bis-(isothiuronium trifluoroacetate) and 2-(tribromomethylsulphonyl)benzothiazole); and merocyanine dyes such as 3-ethyl-5[(3-ethyl-2-benzothiazolinylidene)-1-methylethylidene]-2-thio-2,4-oxazolidinedione; phthalazinone, phthalazinone derivatives or metal salts or these derivatives such as 4-(1-naphthyl)phthalazinone, 6-chlorophthalazinone, 5,7-dimethoxyphthalazinone, and 2,3-dihydro-1,4-phthalazinedione; a combination of phthalazinone plus sulphinic acid derivatives, e.g., phthalic acid, 4-methylphthalic acid, 4-nitrophthalic acid, and tetrachlorophthalic anhydride; quinazolinediones, benzoxazine or naphthoxazine derivatives; rhodium complexes functioning not only as tone modifiers but also as sources of halide ion for silver halide formation in situ, such as ammonium hexachlororhodate (III), rhodium bromide, rhodium nitrate and potassium hexachlororhodate (III); inorganic peroxides and persulphates, e.g., ammonium peroxydisulphate and hydrogen peroxide; benzoxazine-2,4-diones such as 1,3-benzoxazine-2,4-dione, 8-methyl-1,3-benzoxazine-2,4-dione, and 6-nitro-1,3-benzoxazine-2,4-dione; pyrimidines and asym-triazines, e.g., 2,4-dihydroxypyrimidine, 2-hydroxy-4-aminopyrimidine, and azauracil, and tetrazapentalene derivatives, e.g, 3,6-dimercapto-1,4-diphenyl-1H,4H-2,3a,5,6a-tetrazapentalene, and 1,4-di(o-chloro-phenyl)3,6-dimercapto-1H,4H-2,3a,5,6a-tetrazapentalene.

A number of methods have been proposed for obtaining color images with dry silver systems. Such methods include incorporated coupler materials, e.g., a combination of silver benzotriazole, well known magenta, yellow and cyan dye-forming couplers, aminophenol developing agents, a base release agent such as guanidinium trichloroacetate and silver bromide in poly(vinyl butyral); a combination of silver bromoiodide, sulphonamidophenol reducing agent, silver behenate, poly(vinyl butyral), an amine such as n-octadecylamine and 2-equivalent or 4-equivalent cyan, magenta or yellow dye-forming couplers; incorporating leuco dye bases which oxidizes to form a dye image, e.g., Malechite Green, Crystal Violet and pararosaniline; a combination of in situ silver halide, silver behenate, 3-methyl-1-phenylpyrazolone and N,N'-dimethyl-p-phenylenediamine hydrochloride; incorporating phenolic leuco dye reducing agents such as 2-(3,5-di-tert-butyl-4-hydroxyphenyl)-4,5-diphenylimidazole, and bis(3,5-di-tert-butyl-4-hydroxyphenyl)phenylmethane, incorporating azomethine dyes or azo dye reducing agents; silver dye bleach process, e.g., an element comprising silver behenate, behenic acid, poly(vinyl butyral), poly(vinylbutyral)peptized silver bromoiodide emulsion, 2,6-dichloro-4-benzenesulphonamidophenol, 1,8-(3,6-diazaoctane)bisisothiuronium-p-toluene sulphonate and an azo dye was exposed and heat processed to obtain a negative silver image with a uniform distribution of dye which was laminated to an acid activator sheet comprising polyacrylic acid, thiourea and p-toluene sulphonic acid and heated to obtain well defined positive dye images; and incorporating amines such as aminoacetanilide (yellow dye-forming), 3,3'-dimethoxybenzidine (blue dye-forming) or sulphanilanilide (magenta dye forming) which react with the oxidized form of incorporated reducing agents such as 2,6-dichloro-4-benzene-sulphonamido-phenol to form dye images. Neutral dye images can be obtained by the addition of amines such as behenylamine and p-anisidine.

Leuco dye oxidation in such silver halide systems are disclosed in U.S. Pat. Nos. 4,021,240, 4,374,821, 4,460,681 and 4,883,747.

Silver halide emulsions containing the stabilizers of this invention can be protected further against the additional production of fog and can be stabilized against loss of sensitivity during keeping. Suitable anti-foggants and stabilizers which can be used alone or in combination, include the thiazolium salts described in Staud, U.S. Pat. No. 2,131,038 and Allen U.S. Pat. No. 2,694,716; the azaindenes described in Piper, U.S. Pat. No. 2,886,437 and Heimbach, U.S. Pat. No. 2,444,605; the mercury salts described in Allen, U.S. Pat. No. 2,728,663; the urazoles described in Anderson, U.S. Pat. No. 3,287,135; the sulfocatechols described in Kennard, U.S. Pat. No. 3,235,652; the oximes described in Carrol et. al., British Patent No. 623,448; nitron; nitroindazoles; the polyvalent metal salts described in Jones, U.S. Pat. No. 2,839,405; the thiuronium salts described by Herz, U.S. Pat. No. 3,220,839; and palladium, platinum and gold salts described in Trivelli, U.S. Pat. No. 2,566,263 and Damschroder, U.S. Pat. No. 2,597,915.

Stabilized emulsions of the invention can contain plasticizers and lubricants such as polyalcohols, e.g., glycerin and diols of the type described in Milton, U.S. Pat. No. 2,960,404; fatty acids or esters such as those described in Robins, U.S. Pat. No. 2,588,765 and Duane, U.S. Pat. No. 3,121,060; and silicone resins such as those described in DuPont British Patent No. 955,061.

The photothermographic elements can include image dye stabilizers. Such image dye stabilizers are illustrated by U.K. Patent No. 1,326,889; Lestina et al. U.S. Pat. Nos. 3,432,300 and 3,698,909; Stern et al. U.S. Pat. No. 3,574,627; Brannock et al. U.S. Pat. No. 3,573,050; Arai et al. U.S. Pat. No. 3,764,337 and Smith et al. U.S. Pat. No. 4,042,394.

Photothermographic elements containing emulsion layers stabilized according to the present invention can be used in photographic elements which contain light absorbing materials and filter dyes such as those described in Sawdey, U.S. Pat. No. 3,253,921; Gaspar U.S. Pat. No. 2,274,782; Carroll et al., U.S. Pat. No. 2,527,583 and Van Campen, U.S. Pat. No. 2,956,879. If desired, the dyes can be mordanted, for example, as described in Milton and Jones, U.S. Pat. No. 3,282,699.

Photothermographic elements containing emulsion layers stabilized as described herein can contain matting agents such as starch, titanium dioxide, zinc oxide, silica, polymeric beads including beads of the type described in Jelley et al., U.S. Pat. No. 2,992,101 and Lynn, U.S. Pat. No. 2,701,245.

Emulsions stabilized in accordance with this invention can be used in photothermographic elements which contain antistatic or conducting layers, such as layers that comprise soluble salts, e.g., chlorides, nitrates, etc., evaporated metal layers, ionic polymers such as those described in Minsk, U.S. Pat. Nos. 2,861,056, and 3,206,312 or insoluble inorganic salts such as those described in Trevoy, U.S. Pat. No. 3,428,451.

The binder may be selected from any of the well-known natural or synthetic resins such as gelatin, polyvinyl acetals, polyvinyl chloride, polyvinyl acetate, cellulose acetate, polyolefins, polyesters, polystyrene, polyacrylonitrile, polycarbonates, and the like. Copolymers and terpolymers are of course included in these definitions. The preferred photothermographic silver containing polymer is polyvinyl butyral, butethyl cellulose, methacrylate copolymers, maleic anhydride ester copolymers, polystyrene, and butadiene-styrene copolymers.

Optionally these polymers may be used in combination of two or more thereof. Such a polymer is used in an amount sufficient to carry the components dispersed therein, that is, within the effective range of the action as the binder. The effective range can be appropriately determined by one skilled in the art. As a guide in the case of carrying at least an organic silver salt, it can be said that a preferable ratio of the binder to the organic silver salt ranges from 15:1 to 1:2, and particularly from 8:1 to 1:1.

Photothermographic emulsions containing the stabilizer of the invention can be coated on a wide variety of supports. Typical supports include polyester film, subbed polyester film, poly(ethylene terephthalate)film, cellulose nitrate film, cellulose ester film, poly(vinyl acetal) film, polycarbonate film and related or resinous materials, as well as glass, paper metal and the like. Typically, a flexible support is employed, especially a paper support, which can be partially acetylated or coated with baryta and/or an alphaolefin polymer, particularly a polymer of an alpha-olefin containing 2 to 10 carbon atoms such as polyethylene, polypropylene, ethylenebutene copolymers and the like.

The substrate with backside resistive heating layer may also be used in color photothermographic imaging systems such as shown in U.S. Pat. Nos. 4,460,681 and 4,374,921.

Photothermographic emulsions of this invention can be coated by various coating procedures including dip coating, air knife coating, curtain coating, or extrusion coating using hoppers of the type described in Benguin, U.S. Pat. No. 2,681,294. If desired, two or more layers may be coated simultaneously by the procedures described in Russell, U.S. Pat. No. 2,761,791 and Wynn British Patent No. 837,095.

The present invention will be illustrated in detail in reference to the following examples, but the embodiment of the present invention is not limited thereto.

EXAMPLE 1

A dispersion of silver behenate half soap was made at 10% solids in toluene and acetone by homogenization. To 127 g of this silver half soap dispersion was added 252 g methyl ethyl ketone and 104 g isopropyl alcohol. After 15 minutes of mixing, 4 ml of mercuric bromide (.36/10 ml methanol) were added. Then 8.0 ml of calcium bromide (.236 g/10ml methanol) was added 30 minutes later. After two hours of mixing, 27.0 g of polyvinylpyrrolidone was added, and 27.0 g of polyvinylbutyral was added one hour later.

To 32.1 g of the prepared silver premix described above was added 2.0 ml of the sensitizing dye A (0.045 g/50ml of methanol) shown below.

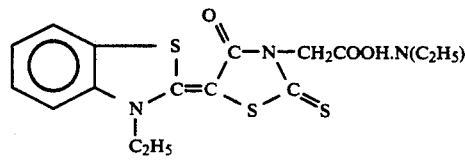

After 20 minutes, a yellow color-forming leuco dye solution was added as shown below.

| Component | Amount |
| --- | --- |
| Leuco Dye B | .275 g |
| Tribenzylamine | .24 g |
| Phthalazinone | .14 g |
| Tetrahydrofuran | 6.0 ml |

The leuco dye is disclosed in U.S. Pat. No. 4,883,747 and has the following formula:

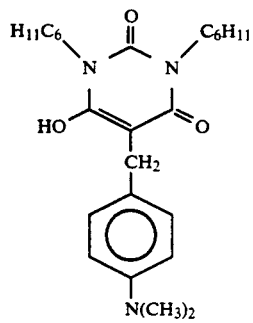

B

After sensitization with the dye and the addition of the leuco base dye solution, Compound I-A was added in the amounts of 0.25 ml or 0.5 ml at a concentration of 0.03 g/5 ml of methanol to a 9.9 g aliquot of the yellow coating solution. The resulting solutions were coated along with an unstabilized solution at a wet thickness of 3 mils and dried at 82° C. in an oven for 5 minutes onto a vesicular polyester base. A topcoat solution was coated at a wet thickness of 3 mils and dried at 82° C. in an oven for 5 minutes over the silver halide layer. The topcoat solution consisted of 7% polyvinyl alcohol in an approximate 50:50 mixture of water and methanol and 0.2 % phthalazine.

The samples were exposed for $10^{-3}$ seconds through a 47B Wratten filter and a 0 to 3 continuous wedge and developed by heating to approximately 138° C. for 6 seconds.

The density of the dye for each sample was measured using a blue filter of a computer densitometer. Post-processing stability was measured by exposing imaged samples to 1200 ft-candles of illumination for 6 hours at 65% relative humidity and 26.7° C. The initial sensitometric data are shown below:

|  | Dmin | Dmax | Speed[1] | Contrast[2] |
| --- | --- | --- | --- | --- |
| Control (0.0 ml I-A) | .12 | 2.55 | 1.83 | 4.72 |
| 0.25 ml I-A | .13 | 2.47 | 1.83 | 5.01 |
| 0.5 ml I-A | .12 | 2.43 | 1.90 | 4.80 |

[1]Log exposure corresponding to density of 0.6 above Dmin.
[2]Average contrast measured by the slope of the line joining density points 0.3 and 0.9 above Dmin.

The post-processing print stability results are shown below:

|  | ΔDmin | ΔDmax |
| --- | --- | --- |
| Control (0.0 ml I-A) | +.60 | −.20 |
| 0.25 ml I-A | +.39 | −.23 |
| 0.5 ml I-A | +.40 | −.23 |

At these concentrations, initial sensitometry was not affected and a 35% Dmin post-processing improvement vs. the unstabilized control was observed.

EXAMPLE 1A (Comparison)

To 9.9 g of the yellow silver halide coating solution as described in Example 1 was added 0.25 ml or 0.5 ml of compound I-A at a concentration of 0.03 g/5 ml methanol; or 0.2 ml or 0.5 ml or 1.0 ml of 3,4-dimethyl-5-mercapto-1,2,4-triazole (DMT) at a concentration of 0.021 g/10 ml methanol. The silver solutions and topcoats were coated, exposed and processed as described in Example 1. The initial sensitometric data is shown below.

|  | Dmin | Dmax | Speed[1] | Contrast[2] |
| --- | --- | --- | --- | --- |
| Control (0.0 ml) | .11 | 2.32 | 1.87 | 4.91 |
| 0.2 ml DMT | .11 | 2.32 | 1.93 | 5.23 |
| 0.5 ml DMT | .11 | 2.31 | 2.10 | 5.11 |
| 1.0 ml DMT | .10 | 2.20 | 2.31 | 4.94 |
| 0.25 ml I-A | .11 | 2.32 | 1.83 | 5.12 |
| 0.5 ml I-A | .10 | 2.15 | 1.90 | 4.13 |

[1]Log exposure corresponding to density of 0.6 above Dmin.
[2]Average contrast measured by the slope of the line joining density points 0.3 and 0.9 above Dmin.

The post-processing print stability was measured as described in Example 1 and the results are shown below.

|  | ΔDmin | ΔDmax |
| --- | --- | --- |
| Control (0.0 ml) | +.53 | −.10 |
| 0.2 ml DMT | +.50 | −.08 |
| 0.5 ml DMT | +.50 | −.13 |
| 1.0 ml DMT | +.37 | −.18 |
| 0.25 ml I-A | +.35 | −.09 |
| 0.5 ml I-A | +.25 | −.15 |

At the 0.5 ml addition of DMT, desensitization of the silver halide emulsion has occured and no post-processing Dmin improvement was observed. However, at the same molar concentration for I-A (0.25 ml), no desensitization had occurred and a 34% post-processing Dmin improvement was observed.

EXAMPLE 1-B (COMPARISON)

To 9.9 g of the yellow silver halide coating solution as described in Example 1 was added 0.2 ml or 1.0 ml or 5-mercapto-1,2,4 triazole (MT) at a concentration of 0.1 g/5 ml methanol. The silver solutions and top coats were coated, exposed and processed as described in Example 1. The initial sensitometric data is shown below.

|  | Dmin | Dmax | Speed[1] | Contrast[2] |
| --- | --- | --- | --- | --- |
| Control (0.0 ml) | .14 | 2.44 | 1.96 | 6.12 |
| 0.2 ml MT | .12 | .59 | — | — |
| 1.0 ml MT | .14 | .15 | — | — |

[1]Log exposure corresponding to density of 0.6 above Dmin.
[2]Average contrast measured by the slope of the line joining density points 0.3 and 0.9 above Dmin.

The post-processing print stability was measured as described in Example 1 and the results are shown below.

|  | ΔDmin | ΔDmax |
|---|---|---|
| Control (0.0 ml) | +.52 | −.17 |
| 0.2 ml MT | +.43 | — |
| 1.0 ml MT | +.13 | — |

At the 0.2 ml addition of MT, in which great desensitization of the silver halide emulsion has occurred, very little post-processing Dmin improvement was observed.

EXAMPLE 1-C (COMPARISON)

To 9.9 g of a yellow silver coating solution similar to Example 1, was added 0.3 ml or 0.9 ml of 3-methyl-5-mercapto-1,2,4-triazole (MMT) at a concentration of 0.013 g/5 ml of ethanol and coated as described in Example 1. A similar topcoat was coated over the yellow silver layer as described in Example 1. The samples were exposed and processed as described in Example 1, and the initial sensitometric data is shown below.

|  | Dmin | Dmax | Speed[1] | Contrast[2] |
|---|---|---|---|---|
| Control (0.0 ml) | .12 | 2.49 | 1.86 | 4.09 |
| 0.3 ml MMT | .11 | 2.31 | 2.11 | 4.09 |
| 0.9 ml MMT | .11 | 1.29 | 2.66 | 3.01 |

[1]Log exposure corresponding to density of 0.6 above Dmin.
[2]Average contrast measured by the slope of the line joining density points 0.3 and 0.9 above Dmin.

The post-processing print stability was measured as described in Example 1 and the results are shown below.

|  | ΔDmin | ΔDmax |
|---|---|---|
| Control (0.0 ml) | +.56 | −.11 |
| 0.3 ml MMT | +.49 | −.11 |
| 0.9 ml MMT | +.27 | −.10 |

At the 0.3 ml addition of MMT in which desensitization has occurred, very little post-processing Dmin improvement was observed.

EXAMPLE 2

A two color formulation was tested with compound I-A. To 9.9 g of the yellow silver halilde dispersion described in Example 1 was added 0.2 ml or 0.5 ml of compound I-A at a concentration of 0.05 g/5 ml in methanol. The resulting solutions and an unstabilized silver halide dispersion were coated with a topcoat as described in Example 1. In addition to the yellow silver halide layer and topcoat layers, a third coating solution was prepared by using 502 g of the silver half soap dispersion of Example 1. After 15 minutes of mixing, a 0.5 g/9.75 g mercuric acetate in methanol solution and a 0.55 g/18.4 g calcium bromide in methanol solution were added. Then an additional 0.55 g/18.4 g calcium bromide in methanol solution was added 30 minutes later. After 45 minutes of mixing, 49.8 g of polyvinylbutyral was added.

To 35.8 g of prepared silver premix described above was added 1.4 ml of the sensitizing dye c (0.021 g/100 ml of methanol) shown below.

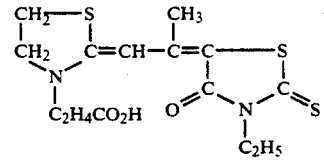

After 30 minutes, a magenta color-forming leuco dye solution was added as shown below.

| Component | Amount |
|---|---|
| Leuco Dye D. | .593 g |
| Phthalazinone | .901 g |
| Tetrahydrofuran | 47.6 g |
| VAGH (Union Carbide) | 2.2 g |
| Polyvinylbutyral | 10.2 g |

The leuco dye is disclosed in U.S. Pat. No. 4,795,697 and has the following formula:

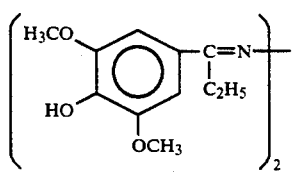

A fourth layer topcoat solution was prepared consisting of 24.0% polystyrene resin in approximately 52% tetrahydrofuran, 17% toluene, 2% acetone and 5% methanol.

The third and fourth layers are coated simultaneously onto the yellow topcoat at 2 mils wet thickness, respectively, and dried 5 minutes at 82° C. The samples were exposed and processed as described in Example 1. The initial sensitometric data is shown below for the bipack.

|  | Dmin | Dmax | Speed[1] | Contrast[2] |
|---|---|---|---|---|
| Control (0.0 ml) | .17 | 1.62 | 1.83 | 2.87 |
| 0.2 ml I-A | .16 | 1.66 | 1.82 | 2.90 |
| 0.5 ml I-A | .16 | 1.65 | 1.90 | 2.85 |

[1]Log exposure corresponding to density of 0.6 above Dmin.
[2]Average contrast measured by the slope of the line joining density points 0.3 and 0.9 above Dmin.

The post processing print stability results as tested in Example 1 are shown below.

|  | ΔDmin | ΔDmax |
|---|---|---|
| Control (0.0 ml) | +.50 | 0 |
| 0.2 ml I-A | +.41 | −.02 |
| 0.5 ml I-A | +.26 | −.06 |

The addition of I-A to the yellow silver layer had no effect on initial sensitometric responses of the magenta color forming layer. A 48% Dmin post-processing improvement vs. the unstabilized sample was observed for the yellow silver layer without any effects on the initial sensitometric responses.

EXAMPLE 3

To 9.9 g of a yellow silver halide solution as described in Example 1 was added 0.1 ml or 0.35 ml or 1.0 ml of compound I-A at a concentration of 0.015 g/25 ml of methanol. A similar topcoat was prepared as described in Example 1. A magenta silver halide coating solution and topcoat were also prepared as described in Example 2 for a two color formulation. The exposure and processing were the same as in Example 1, and the initial sensitometric responses are shown below for the bipacks.

|  | Dmin | Dmax | Speed[1] | Contrast[2] |
| --- | --- | --- | --- | --- |
| Control (0.0 ml) | .18 | 1.56 | 2.05 | 2.25 |
| 0.1 ml I-A | .19 | 1.61 | 2.04 | 2.39 |
| 0.35 ml I-A | .18 | 1.60 | 2.07 | 2.28 |
| 1.0 ml I-A | .18 | 1.60 | 2.05 | 2.25 |

[1]Log exposure corresponding to density of 0.6 above Dmin.
[2]Average contrast measured by the slope of the line joining density points 0.3 and 0.9 above Dmin.

Unexposed stability was tested by pre-equilibrating unexposed samples for 16 hours at 22° C. and 50% relative humidity, then sealing the samples in a foil bag and placing in an oven at 50° C. for 8 hours. These results are shown below.

|  | Shelf Life | |
| --- | --- | --- |
|  | ΔDmin | ΔDmax |
| Control (0.0 ml) | +.42 | −.04 |
| 0.1 ml I-A | +.43 | −.06 |
| 0.35 ml I-A | +.28 | −.05 |
| 1.0 ml I-A | +.19 | −.01 |

The results show an improvement in the unexposed Dmin without any effects on the initial sensitometric responses.

What is claimed is:

1. A photothermographic imaging element comprising a substrate having on at least one side thereof a layer comprising a photographic silver halide in reactive association with a silver source material, a reducing agent for silver ion, and a binder, said layer having therein or in an adjacent layer a post processing stabilizing amount of an electron-withdrawing group at least as electron-withdrawing as $CF_3(CH_2)_6-$ on the 3-position of 5-mercapto-1,2,4-triazole wherein said triazole is represented by the formula:

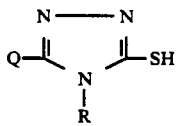

wherein
R represents hydrogen, alkyl group, aryl group or aralkyl group, and
Q represents an electron-withdrawing group at least as electron-withdrawing as $CF_3(CH_2)_6-$, and wherein Q is represented by the formula:

$$(H)_e (CX_3)_a (CF_2) (CH_2)_d-$$

wherein
X comprises halogen atoms,
a is 0 or 1,
c is 0 or between 1 and 20,
d is 0 or between 1 and 6,
e is 0 when a is 1 and e is 1 when a is 0, and
a plus c is at least 1, 2. The element of claim 1 wherein d and e are zero.
3. The element of claim 1 wherein Q represents a perfluoroalkyl moiety of 1 to 20 carbon atoms.
4. The element of claim 1 wherein X is fluorine.
5. The element of claim 2 wherein X is fluorine.
6. The element of claim 1 wherein X comprises fluorine with a minor proportion of chlorine and/or bromine.
7. The element of claim 1 wherein said triazole is present in said element in an amount of from $10^{-3}$ to 10 mols triazole per mole of silver halide in said element.
8. The element of claim 2 wherein said triazole is present in said element in an amount of from $10^{-3}$ to 10 mols triazole per mole of silver halide in said element.
9. The element of claim 3 wherein said triazole is present in said element in an amount of from $10^{-3}$ to 10 mols triazole per mole of silver halide in said element.
10. The element of claim 4 wherein said triazole is present in said element in an amount of from $10^{-3}$ to 10 mols triazole per mole of silver halide in said element.
11. The element of claim 5 wherein said triazole is present in said element in an amount of from $10^{-3}$ to 10 mols triazole per mole of silver halide in said element.
12. The element of claim 6 wherein said triazole is present in said element in an amount of from $10^{-3}$ to 10 mols triazole per mole of silver halide in said element.
13. The element of claim 12 wherein Q is selected from the group consisting of perfluoroalkyl of 1 to 20 carbon atoms, and perfluoroalkyl of 1 to 20 carbon atoms having a bridging group to the triazole of a polymethine chain of 1 to 6 carbon atoms.
14. The element of claim 10 wherein R is selected from the group consisting of alkyl of 1 to 6 carbon atoms, and phenyl group.
15. The element of claim 13 wherein R is selected from the group consisting of alkyl of 1 to 6 carbon atoms, and phenyl group.

* * * * *

UNITED STATES PATENT AND TRADEMARK OFFICE
CERTIFICATE OF CORRECTION

PATENT NO. : 5,149,620

DATED : Simpson et al.

INVENTOR(S) : Sept. 22, 1992

It is certified that error appears in the above-identified patent and that said Letters Patent is hereby corrected as shown below:

First Page, Inventors, Replace 1st inventors first name from "Sahron" to --Sharon--

Col. 2, line 47, Delete "hd" after --$CF_3(CH_2)$--

Col. 7, line 32, Replace second "2,4-" with --2'4'---

Col. 10, Diagram, "$CH_2COOH.N(C_2H_5)_3$" should be --$CH_2COOH\ N(C_2H_5)_3$--

Col. 13, line 49, Replace "halilde" with --halide--

Col. 13, line 67, Replace "c" with --<u>c</u>--

Col. 14, line 15, Replace "D" with --<u>D</u>--

Col. 14, line 25, Replace "〔 〕" with --( )--

Col. 16, line 8, Replace "$(H)_e(CX_3)_9(CF_2)(CH_2)d$-" with --$(H)_e(CX_3)_9(CF_2)_c(CH_2)d$---

Signed and Sealed this

Ninth Day of November, 1993

*Attest:*

BRUCE LEHMAN

*Attesting Officer*    *Commissioner of Patents and Trademarks*